(12) United States Patent
Kay et al.

(10) Patent No.: US 11,064,904 B2
(45) Date of Patent: Jul. 20, 2021

(54) SMART DRILL, JIG, AND METHOD OF ORTHOPEDIC SURGERY

(71) Applicant: EXTREMITY DEVELOPMENT COMPANY, LLC, Akron, OH (US)

(72) Inventors: David B. Kay, Akron, OH (US); Ian P. Kay, Fairlawn, OH (US); Dustin Ducharme, Littleton, CO (US)

(73) Assignee: EXTREMITY DEVELOPMENT COMPANY, LLC, Akron, OH (US)

( * ) Notice: Subject to any disclaimer, the term of this patent is extended or adjusted under 35 U.S.C. 154(b) by 386 days.

(21) Appl. No.: 15/445,311

(22) Filed: Feb. 28, 2017

(65) Prior Publication Data

US 2017/0245781 A1     Aug. 31, 2017

Related U.S. Application Data

(60) Provisional application No. 62/301,257, filed on Feb. 29, 2016, provisional application No. 62/358,739, filed on Jul. 6, 2016.

(51) Int. Cl.
*A61B 34/20* (2016.01)
*A61B 34/00* (2016.01)
(Continued)

(52) U.S. Cl.
CPC .............. *A61B 5/062* (2013.01); *A61B 5/067* (2013.01); *A61B 5/1121* (2013.01);
(Continued)

(58) Field of Classification Search
CPC .... A61B 2034/2072; A61B 2560/0223; A61B 2562/0219; A61B 34/20; A61B 5/062;
(Continued)

(56) References Cited

U.S. PATENT DOCUMENTS 5,230,338 A    7/1993 Allen et al.
5,230,623 A    7/1993 Guthrie et al.
(Continued)

FOREIGN PATENT DOCUMENTS

CA    2570336 C      1/2013
CN    104271046 A    1/2015
(Continued)

OTHER PUBLICATIONS

Mendes et al., Ethylene oxide sterilization of medical devices: A review, Nov. 2007 (Year: 2007).*
(Continued)

*Primary Examiner* — Luther Behringer
*Assistant Examiner* — Farouk A Bruce
(74) *Attorney, Agent, or Firm* — Hudak, Shunk & Farine Co. LPA

(57) ABSTRACT

The present invention provides a MEMS sensor guidance system mounted on a surgical instrument and uses the MEMS sensor to determine Inertial Measurement Units to track rotation and acceleration in all three spatial directions. Further the invention provides a method of surgery in which a reference axis, a loci, and a depth are defined and the instrument including the sensor cluster of the invention is placed in relation to the y-axis and x-axis and following the working end is aligned and the orientation and depth data display is observed to aid in maintaining the desired instrument.

31 Claims, 10 Drawing Sheets

(51) Int. Cl.
*A61B 34/10* (2016.01)
*A61B 5/06* (2006.01)
*A61B 90/00* (2016.01)
*A61B 5/11* (2006.01)
*A61B 17/17* (2006.01)
*A61B 5/00* (2006.01)

(52) U.S. Cl.
CPC .......... *A61B 5/1127* (2013.01); *A61B 17/17* (2013.01); *A61B 34/20* (2016.02); *A61B 34/25* (2016.02); *A61B 90/37* (2016.02); *A61B 5/0035* (2013.01); *A61B 5/743* (2013.01); *A61B 2034/107* (2016.02); *A61B 2034/2048* (2016.02); *A61B 2034/2072* (2016.02); *A61B 2505/05* (2013.01); *A61B 2560/0223* (2013.01); *A61B 2562/028* (2013.01); *A61B 2562/0219* (2013.01)

(58) Field of Classification Search
CPC ..... A61B 5/067; A61B 5/1071; A61B 5/1072; A61B 5/1121; A61B 5/1127; A61B 5/743; A61B 5/746; A61B 90/37; A61B 2034/2048
See application file for complete search history.

(56) References Cited

U.S. PATENT DOCUMENTS

| | | | |
|---|---|---|---|
| 5,724,264 A | 3/1998 | Rosenberg et al. | |
| 5,957,934 A | 9/1999 | Rapoport | |
| 5,980,526 A * | 11/1999 | Johnson | A61B 17/152 606/86 R |
| 6,019,724 A | 2/2000 | Gronningsaeter et al. | |
| 6,711,432 B1 | 3/2004 | Krause et al. | |
| 6,725,082 B2 | 4/2004 | Sati et al. | |
| 6,785,571 B2 * | 8/2004 | Glossop | A61B 90/36 600/424 |
| 6,980,849 B2 | 12/2005 | Sasso | |
| 7,073,271 B2 | 7/2006 | Raab et al. | |
| 7,217,276 B2 | 5/2007 | Henderson et al. | |
| 7,302,288 B1 | 11/2007 | Schellenberg | |
| 7,427,200 B2 | 9/2008 | Noble et al. | |
| 7,458,977 B2 | 12/2008 | McGinley et al. | |
| 7,586,546 B2 | 9/2009 | Lee et al. | |
| 7,771,436 B2 | 8/2010 | Moctezuma de la Barrera et al. | |
| 7,840,254 B2 | 11/2010 | Glossop | |
| 8,073,528 B2 | 12/2011 | Zhao et al. | |
| 8,114,086 B2 | 2/2012 | Claypool et al. | |
| 8,147,503 B2 | 4/2012 | Zhao et al. | |
| 8,165,658 B2 | 4/2012 | Waynik et al. | |
| 8,167,823 B2 | 5/2012 | Nycz et al. | |
| 8,442,621 B2 | 5/2013 | Gorek et al. | |
| 8,491,579 B2 | 7/2013 | Rossetto | |
| 8,516,711 B2 | 8/2013 | Pettersson | |
| 8,709,016 B2 | 4/2014 | Park et al. | |
| 8,832,954 B2 | 9/2014 | Atwell et al. | |
| 8,961,537 B2 | 2/2015 | Leung et al. | |
| 9,119,572 B2 | 9/2015 | Gorek et al. | |
| 9,144,470 B2 | 9/2015 | Proulx et al. | |
| 9,179,987 B2 | 11/2015 | Goodacre | |
| 9,283,047 B2 | 3/2016 | Namiki | |
| 9,283,048 B2 | 3/2016 | Kostrzewski et al. | |
| 9,341,704 B2 | 5/2016 | Picard et al. | |
| 9,351,782 B2 | 5/2016 | Stein et al. | |
| 9,452,023 B2 | 9/2016 | Boillot et al. | |
| 9,510,771 B1 * | 12/2016 | Finley | A61B 5/743 |
| 9,532,839 B2 | 1/2017 | Seo | |
| 9,554,812 B2 | 1/2017 | Inkpen et al. | |
| 9,561,082 B2 | 2/2017 | Yen et al. | |
| 9,636,185 B2 | 5/2017 | Quaid et al. | |
| 9,639,156 B2 | 5/2017 | Iorgulescu et al. | |
| 9,662,179 B2 | 5/2017 | Nam et al. | |
| 9,706,948 B2 | 7/2017 | Bhandari | |
| 9,707,043 B2 | 7/2017 | Bozung | |
| 9,730,608 B2 | 8/2017 | Lugt et al. | |
| 9,750,510 B2 | 9/2017 | Kostrzewski et al. | |
| 9,782,229 B2 | 10/2017 | Crawford et al. | |
| 9,925,013 B2 | 3/2018 | Dell et al. | |
| 9,964,398 B2 | 5/2018 | Becker et al. | |
| 9,974,613 B2 | 5/2018 | Kang et al. | |
| 9,986,768 B2 | 6/2018 | Force | |
| 10,004,609 B2 | 6/2018 | Palmatier et al. | |
| 10,018,706 B2 | 7/2018 | Cisi | |
| 10,034,713 B2 | 7/2018 | Yang et al. | |
| 10,058,338 B2 | 8/2018 | Shoham | |
| 10,080,617 B2 | 9/2018 | Haider et al. | |
| 10,105,149 B2 | 10/2018 | Haider et al. | |
| 10,136,952 B2 | 11/2018 | Couture et al. | |
| 10,176,625 B2 | 1/2019 | Bridges | |
| 10,194,990 B2 | 2/2019 | Amanatullah et al. | |
| 10,299,874 B2 | 5/2019 | Weitzner et al. | |
| 10,350,014 B2 | 7/2019 | Beelen et al. | |
| 10,357,184 B2 | 7/2019 | Crawford et al. | |
| 10,368,878 B2 | 8/2019 | Lavallee et al. | |
| 10,531,926 B2 | 1/2020 | Roessler | |
| 2003/0059097 A1 * | 3/2003 | Abovitz | A61B 34/20 382/132 |
| 2004/0243148 A1 | 12/2004 | Wasielewski | |
| 2005/0020909 A1 * | 1/2005 | Moctezuma de la Barrera | A61B 17/62 600/424 |
| 2006/0142657 A1 * | 6/2006 | Quaid | A61B 17/1703 600/424 |
| 2006/0173291 A1 * | 8/2006 | Glossop | A61B 90/96 600/424 |
| 2007/0249986 A1 | 10/2007 | Smego | |
| 2007/0270686 A1 * | 11/2007 | Ritter | A61B 34/20 600/424 |
| 2007/0287911 A1 | 12/2007 | Haid et al. | |
| 2009/0177081 A1 * | 7/2009 | Joskowicz | A61B 34/20 600/426 |
| 2011/0275957 A1 * | 11/2011 | Bhandari | A61B 34/20 600/595 |
| 2012/0071757 A1 | 3/2012 | Salcudean et al. | |
| 2012/0203092 A1 | 8/2012 | Sweeney et al. | |
| 2012/0319859 A1 | 12/2012 | Taub et al. | |
| 2012/0330367 A1 | 12/2012 | Roche et al. | |
| 2013/0016185 A1 | 1/2013 | Stolka et al. | |
| 2013/0132026 A1 | 5/2013 | Lippuner et al. | |
| 2013/0165947 A1 | 6/2013 | Nguyen et al. | |
| 2013/0169423 A1 * | 7/2013 | Iorgulescu | G06F 3/016 340/407.1 |
| 2013/0172907 A1 | 7/2013 | Harris | |
| 2014/0107471 A1 * | 4/2014 | Haider | A61B 17/1703 600/424 |
| 2014/0148808 A1 * | 5/2014 | Inkpen | G01B 7/003 606/80 |
| 2014/0163557 A1 | 6/2014 | Beyar et al. | |
| 2014/0276871 A1 | 9/2014 | Sherman et al. | |
| 2015/0355310 A1 | 12/2015 | Gong et al. | |
| 2016/0022374 A1 | 1/2016 | Haider et al. | |
| 2016/0119529 A1 | 4/2016 | Stolka et al. | |
| 2016/0166338 A1 | 6/2016 | Hartmann et al. | |
| 2016/0191887 A1 * | 6/2016 | Casas | H04N 13/279 348/47 |
| 2016/0220320 A1 | 8/2016 | Crawford et al. | |
| 2016/0220385 A1 * | 8/2016 | Falardeau | A61F 2/4609 |
| 2016/0242934 A1 * | 8/2016 | van der Walt | A61B 34/20 |
| 2016/0338776 A1 | 11/2016 | Jaramaz et al. | |
| 2016/0357260 A1 | 12/2016 | Raynor et al. | |
| 2017/0245781 A1 | 8/2017 | Kay et al. | |
| 2017/0327371 A1 * | 11/2017 | Bai | H04W 4/029 |
| 2018/0064496 A1 | 3/2018 | Hladio et al. | |
| 2018/0242967 A1 | 8/2018 | Meade | |

FOREIGN PATENT DOCUMENTS

| | | |
|---|---|---|
| CN | 104656095 A | 5/2015 |
| DE | 10333012 B2 | 5/2007 |
| EP | 0730210 B1 | 6/2002 |
| EP | 1570782 A2 | 7/2005 |
| JP | 4265698 B2 | 5/2009 |

(56) References Cited

FOREIGN PATENT DOCUMENTS

| | | |
|---|---|---|
| JP | 5763666 B2 | 4/2013 |
| JP | 6370789 B2 | 12/2015 |
| WO | 2009027191 A1 | 3/2009 |
| WO | 2015085011 A9 | 6/2015 |
| WO | 2020160120 A1 | 8/2020 |
| WO | 2020172397 A1 | 8/2020 |

OTHER PUBLICATIONS

Andres et al., Laser-guided lumbar medial branch kryorhizotomy, Sep. 2010 (Year: 2010).*
Ajuied et al., "Saw Cut Accuracy in Knee Arthroplasty—An Expiremental Case-Control Study", Journal of Arthritis; pp. 1-5, vol. 4, Issue 1; Published 2015.
International Search Report and Written Opinion dated May 29, 2020.
International Search Report and Written Opinion dated Jun. 22, 2020.

\* cited by examiner

SMART DRILL, JIG, AND METHOD OF ORTHOPEDIC SURGERY

FIELD OF THE INVENTION

This present invention relates to a surgical instrument, which uses a novel surgical guidance system including a microprocessor having memory loaded with appropriate software and one or more sensors in order to track and/or recommend the orientation and movement over time of a work piece or implant in a surgical field using a locally defined coordinate system such that the surgical guidance system provide surgical assistance by means of a specifically designed graphical user interface on an associated display, to a surgeon at a economically efficient cost. The invention further relates to a method of surgery that uses this instrument and may include information stored in the system memory based on generalized information, such as the location of openings in implants or preferred angles for insertion or incision, or on information which is specific to particular patient anatomy or surgical need. In a further embodiment, the invention relates to an aid or jig that is used to define the local coordinate system.

BACKGROUND OF THE INVENTION

Surgeons, and in particular orthopedic surgeons have become accustomed to the use during surgery of mechanical devices, which act to aid the surgeons in their work. Such devices include, for example, depth and drill guides, and jigs, which help the surgeon to align fasteners with bone and with openings in implants so as to provide for the optimal alignment in the bone/implant/fastener construct. This is particularly important in instances where fastener seats first in the bone, and then locks, such as through a threaded relationship with the implant.

Recent developments in surgery recognize the advantage of a surgical approach, which is less invasive than previous techniques, which required relatively large incisions to provide open access to the ultimate surgical field or work site. These relatively new "minimally invasive" procedures work through small incisions, and may even call for procedures to be performed percutaneously, or through the skin. Such approaches provide less insult to the surgical environment, and therefore result in shorter healing times, and ultimately better surgical outcomes. However, they also result in a more limited surgical visibility of the area where the surgeon may be developing a construct including for example, the bone, fasteners, and an implant. Consequently, device developers have designed mechanical means, such as jigs and guides, which help to locate components of the construct during surgical implantation (for example by providing a template for the implant system) in a minimally invasive procedure, including related fasteners or surgical aids such as k-wires. While these means do provide additional guidance, they tend to be awkward to use, and to obscure the surgical view in their own way. Moreover, they are limited to a particular placement and orientation, and do not assist in the variable location in space over time of a component of the construct (for example, they can not account for the reduction of a bone fragment which may change the desirable location of a fastener within that bone fragment.)

Partly in response to trends in surgery realizing the value of electronic assistance, and partly as hardware and software systems have developed to provide medical applications and increased accessibility, surgical navigation systems and robotic devices have been developed to provide increased electro/mechanical assistance to surgeons. Current surgical navigations systems utilize a vast array of complex sensors and imaging systems in order to aid the surgeon in visualizing the real time relative position and orientation of an instrument in 3-dimensional space. They also act in a generally defined global coordinate system which requires rigorous control of the surgical field in relation to that global coordinate system. These surgical navigation systems typically use 3D computer aided tomography and complex imaging functions to allow the surgeons a re-created vision in real-time of the surgical site. Consequently, these systems have extremely high costs to buy and to use (often resulting in institutional ownership such as by the hospital or highly capitalized medical holding groups). Thus, the use of surgical navigation is often limited to certain high margin, high expense and high risk procedures, such as brain or hip replacement surgery and are typically not used by surgeons focused on extremities or by other surgeons, including for example plastic surgeons, podiatrists and oral surgeons.

Moreover, these surgical navigation systems are typically provided in an operating arena that includes complex lighting, monitors, biological function and monitoring systems, and imaging systems and screens such as CT and fluoroscopy systems. While these systems are robustly capable in providing information to the surgeon, the accompanying surgical technique requires the surgeon to rely almost solely on the imaging screen and guide placement, while maintaining more than mere peripheral focus on the actual patient and operating site. This situation constantly requires the surgeon to refocus his or her attention, leading to frustration, muscle strain and fatigue. This increases the potential of complications in the surgery where injury and even loss of life can result from attendant post-operative troubles.

The problem with these surgical navigation systems, apart from the very high cost, is that the system results in inherent distraction due to the layout of the displays. In addition, there is a long learning curve associated with the use of these systems, as well as the cost for the associated CT/MRI data collection required pre-op which tend to limit the application of these systems to high grossing procedures. Although these displays and imaging systems represent "cutting edge" surgical instrumentation and guidance systems, they increase distraction and stress on surgeons by requiring a greater degree of multi-tasking, and intense focus on multiple locations.

The present invention provides an integration of key advantages of these systems into a more "information dense" surgical guidance or "surgical targeting" aid, but one which is within the line of sight of the surgeon as well as the procedure's actual location (i.e. within the actual, not a virtual, patient). In large part, this is due to the compact size of the guidance system, the use of a localized co-ordinate system, the provision of the system display in line with the use of the surgical instrument and in fact, on the instrument itself, and a graphical user interface ("GUI") that is designed to maintain the focus of the surgeon on the location of the instrument and on the work piece as an extension of the instrument, rather than splitting the surgeon's focus onto a displaced screen and the surgical instrument, as well as the actual body area of interest.

This invention uses a six or nine degree of freedom ("DOF") Inertial Measurement Unit (IMU)—to track rotations and accelerations in all three spatial directions by means of using Micro Electrical Mechanical System (MEMS) devices that are cross referenced with a MARG (Magnetic, Angular Rate, and Gravity) sensor, so that 3D spatial orientation and motion can be tracked by converting angular rate to angular position, and acceleration to position through numerical integration. An "LVDT" or linear potentiometer, measures capacitance or inductance that is proportional to physical position to determine position, which could be utilized in order to measure input distances for the system. Thus, the present invention provides a low cost (i.e. having the potential for individual surgeons to own or even for single use) guidance system, which acts as an aid to surgeons, rather than as a substitute for their skills and judgment.

SUMMARY OF THE INVENTION

In accordance with the present invention, a surgical targeting guide is provided which provides a local reference coordinate system defined by the placement of a linear marker, such as a k-wire, and optionally a simple jig to define the optimal placement points, where the guide enhances the surgeon's ability to remain focused and augments his or her skill in operating as per his or her judgment. The invention allows the surgeon to place a sensor and provide [an axis] a vector for a reference position. Thus, the marker or pin is used in which two points are used to define a relative 3-D coordinate system. These two points are at a fixed distance which are known in 3-D and can be used to identify critical features (i.e. biological landmarks) which allows the surgeon to better locate and hold his or her position without the use of cumbersome or fussy jigs and guides.

The guidance system of the present invention includes a 9 degree of freedom (DOF), three axis accelerometer, gyroscope, and magnetometer sensor that could be used to track such motion and orientation (which has a typical retail cost between $15 to $40). This sensor, when integrated into a system that contains a microcontroller and a visual display, could be rigidly attached to the surgeon's drill or saw to provide attitude (i.e., orientation relative to a set of defined axes) and positional guidance during surgery. The display could be attached to the drill or wire guide, or the drill or wire driver, or a cutting tool, such as a saw or burr advantageously with a pattern with a defined entry and exit site. The cutting tool can include electronics and software integrated into the tool with the display through a heads up display such as glasses, and the targeting guide can include safety parameters integrated into the system. The device can be optimized for specific procedures, including for example, hip, knee, and spinal surgeries. The device can be modified to provide the visual representation of a simulated anatomy for use or for training, and the device can be optimized for soft tissue biopsies to minimize the need for CT guided biopsies.

In use, a reference axis is defined along with two relative reference positions, to provide all of the information required to know the dynamics of the system (i.e. surgical instrument orientation and position relative to the reference position and direction determined from the surgery site.) More specifically, the system needs to define, at minimum, three points that do not lie on the same line in order to determine a frame of reference. This can be done by either defining three points in space, two intersecting lines of known length and the point of intersection, or a line of known length and two points (one at the terminal point of the line and one not on the line, where points referring to true positions in a relative reference frame.) Thus, the invention includes a physical, or a virtual jig or template that can use a reference axis, such as is provided by a guide wire implanted at the surgical site, and an orthogonal axis is defined by a point on an arm placed at a right angle to the first axis. In a specific embodiment, a jig encircles the guide wire and has a sliding arm which can be extended along a bone surface and used to define the optimal location of a point at a selectively defined distance from the intersection of the axis at a right angle. Means can also be provide to define horizontal, such as a level bubble, which helps to define the right angle for the second axis.

In order to obtain the real time position, acceleration outputted from the accelerometer is mathematically integrated twice. This integration can compound bias error and begin to accumulate position drift if the error signal is not compensated for. Orientation is obtained from integrating the time rate change of angular position (angular velocity) once to obtain the real time angular position. From these outputs, the difference in the initial angular position and reference position can be shown on the display in order to perform the orientation and positional corrections needed.

The display of the present invention provides a GUI (graphical user interface) comprising a spot on a plot (which is advantageously circular or at least two-dimensional such as referential axes or cross-hatching) where the surgeon has the goal of locating the spot in the plot to cause the instrument (such as a drill or screw driver) to act on axis. A second GUI displays a relative depth such as by a bar graph (for example to locate the distal end of a drill tip or a fastener) so as to provide visual assistance as to the desired amount of penetration.

As a further aspect of the invention, a method of surgery is provided in which relates generally to surgery in which a MEMS sensor guidance system is mounted on an instrument and in the sight line of the surgeon and which uses the MEMS sensor to determine Inertial Measurement Units to track rotation and acceleration in all three spatial directions. In accordance with this method, the surgical area is excised to allow access to the area for surgical intervention and a reference axis is set, for example by drilling a pilot hole, inserting a k-wire such as along an axis which a fastener will intersect and defining a reference axis by registering two points on the k-wire at a known spaced distance. Next, a loci is defined, for example, an entry point for a fastener; and a depth is determined by measuring a boundary distance for the intervention (e.g., when a fastener will be inserted into a bone segment, the thickness of the bone is measured which represents the depth beyond which the surgeon does not wish to penetrate in order to avoid disturbing the soft tissue beyond the cortical surface on the back side of the bone segment). This depth is recorded in a memory of the instrument in accordance with the invention as a value, dy. Next, a value is determined along an orthogonal axis, x, which can be determined using an actual horizontal jig that includes an indication for a fastener entry hole, or a virtual version of the jig which is provided in the microprocessor of the instrument. Then, the instrument including the sensor cluster of the invention is placed in relation to the y-axis and x-axis and the device is calibrated using the button marked "calibrate alignment" on this sensor interface display, after assuring that the axes are properly aligned, for example by checking to be sure that the alignment jig is parallel to the line made with the marked fastener entry location and the centroid axis of the k-wire. The jig can be provided with a sliding arm to define the second point, and with leveling means to ensure the orientation. Then, with the instrument in place, the working end is aligned to the area of intervention, for example, for a drill, the distal end of the drill bit in the drill is aligned to the fastener entry location and the orientation data is displayed on the display screen in the GUI as a green circle, and the fastener orientation is determined and maintained by aligning a fastener icon displayed on the instrument sensor cluster screen in the proper positioning on the alignment marker and by monitoring the degree of work on the secondary work monitor, for example on a graphical representation of the depth or degree of penetration in the Y-axis. This procedure helps to ensure the optimal placement for surgical intervention, for example, for the placement of a pilot hole in order to assure the subsequent alignment and full seating of a fastener, such as a screw having a threaded locking head in relation to a projected internally threaded locking screw hole in an orthopedic implant. As final steps of the method in accordance with the invention, the alignment is repeated as necessary for the placement of all fasteners, and the surgical access or incision is closed. It is also possible to use other means to help define the local coordinate system, such as a beam of light, or other "virtual" templates. Local coordinates can also be obtained from pre-operative CT or MRI scans or intra-operative fluoroscopy. The targeting device helps to keep the surgeon's hand "on target", for example, through the use of a touchscreen in which measurement inputs are placed to define entry and end points with the use algorithms inputted to the IC.

The system includes integral or access to memory (for example in a mobile device, such as a cell phone) which can be programmed for the placement of a plurality of fasteners, or with information that can be general information for specific procedures, such as angles for osteotomies, or can be information relative to individual patients. The method of the present invention is particularly advantageous for use in minimally invasive procedures, and procedures in which fasteners are introduced percutaneously, or through the skin.

DETAILED DESCRIPTION OF THE DRAWINGS

Figure 1:
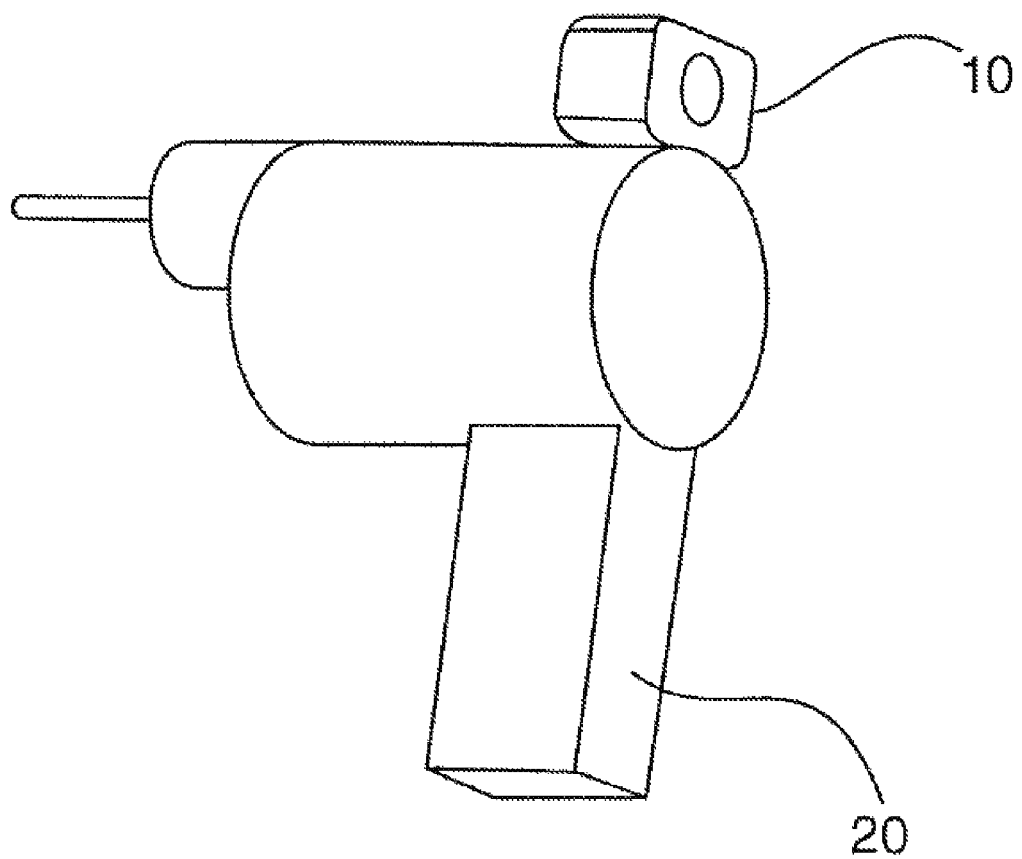
FIG. 1 is side perspective view of a first representation of the surgical guide in accordance with a first embodiment of the present invention.
Figure 2:
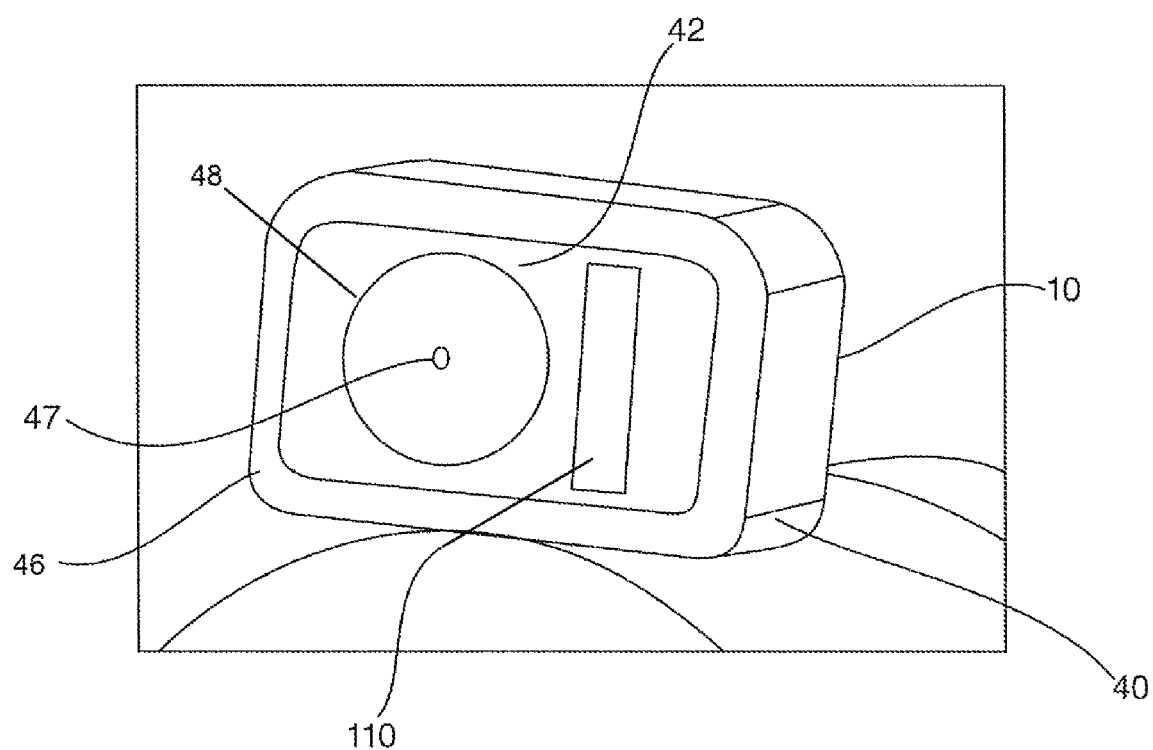
FIG. 2 is a detail of the surgical guide of FIG. 1 showing the display and graphical user interface.
Figure 3:
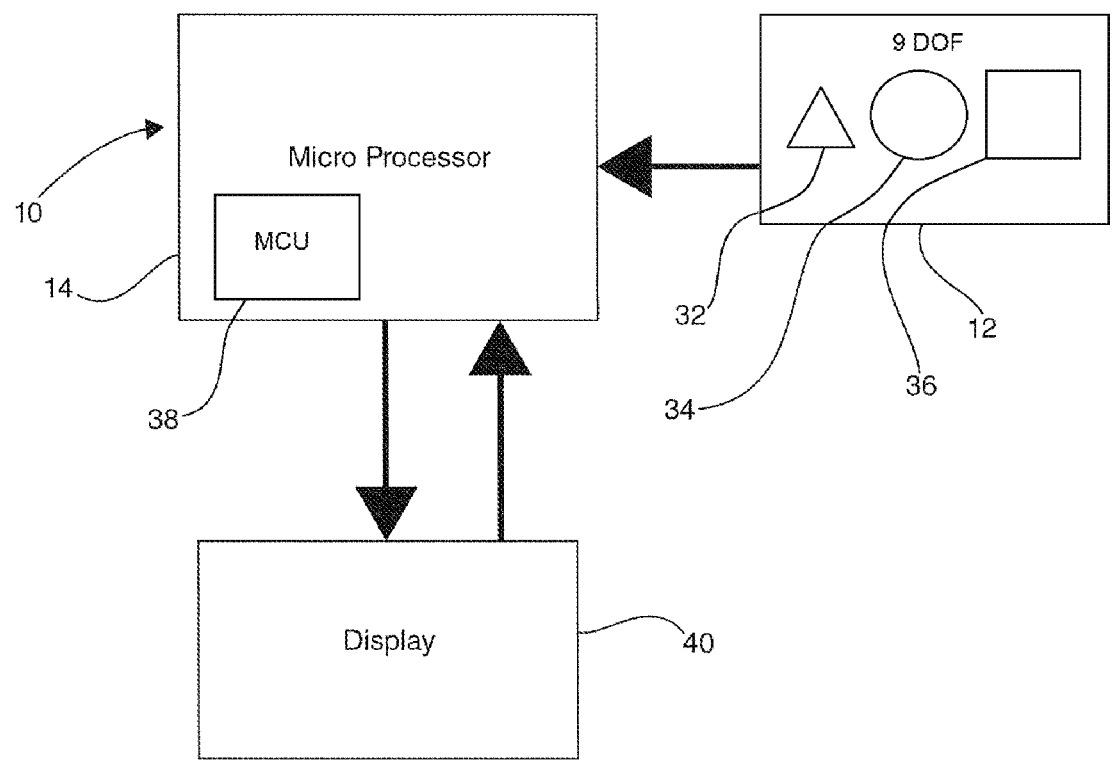
FIG. 3 is a schematic representation of the guidance system in accordance with the invention illustrating the sensor array, which is in communication with the microprocessor, which is in reciprocal communication with the display.
Figure 4:
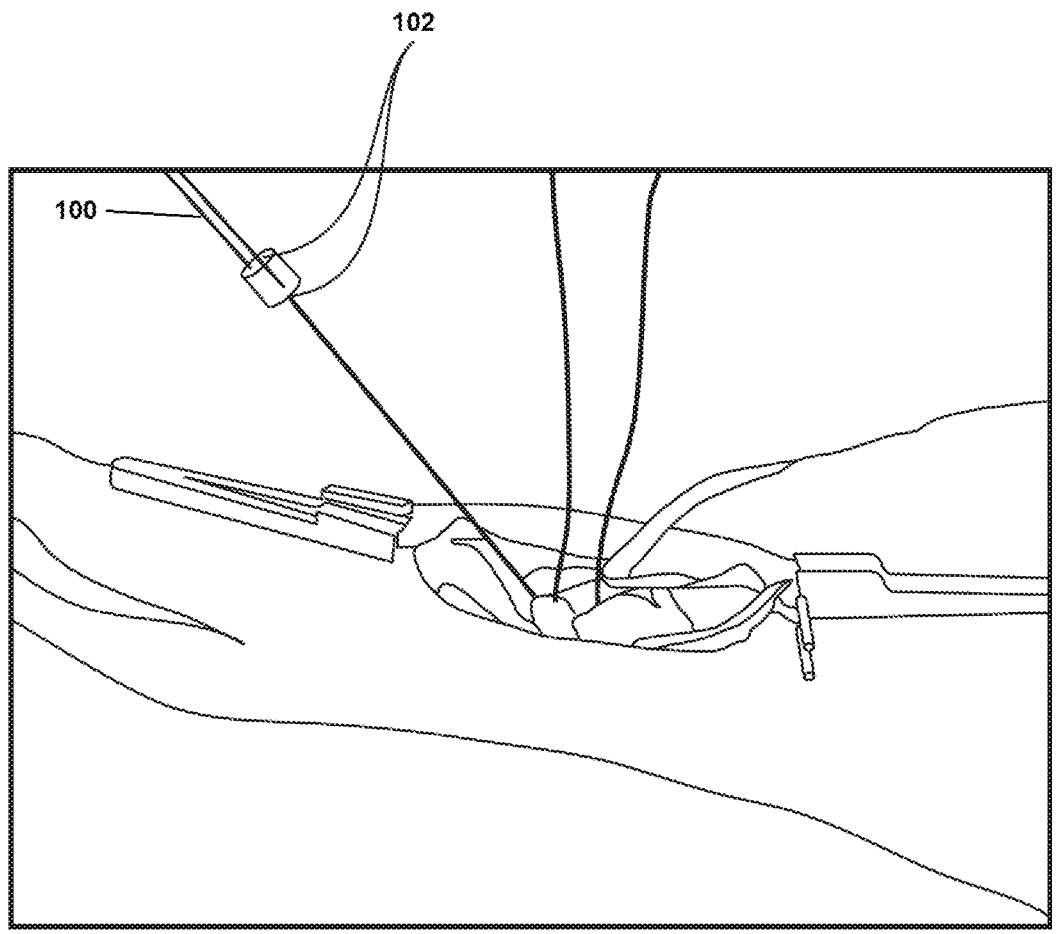
FIG. 4 is a illustration of a set-up for an orthopedic surgery illustrating the use of k-wires or pins to define the reference coordinate system.
Figure 5:
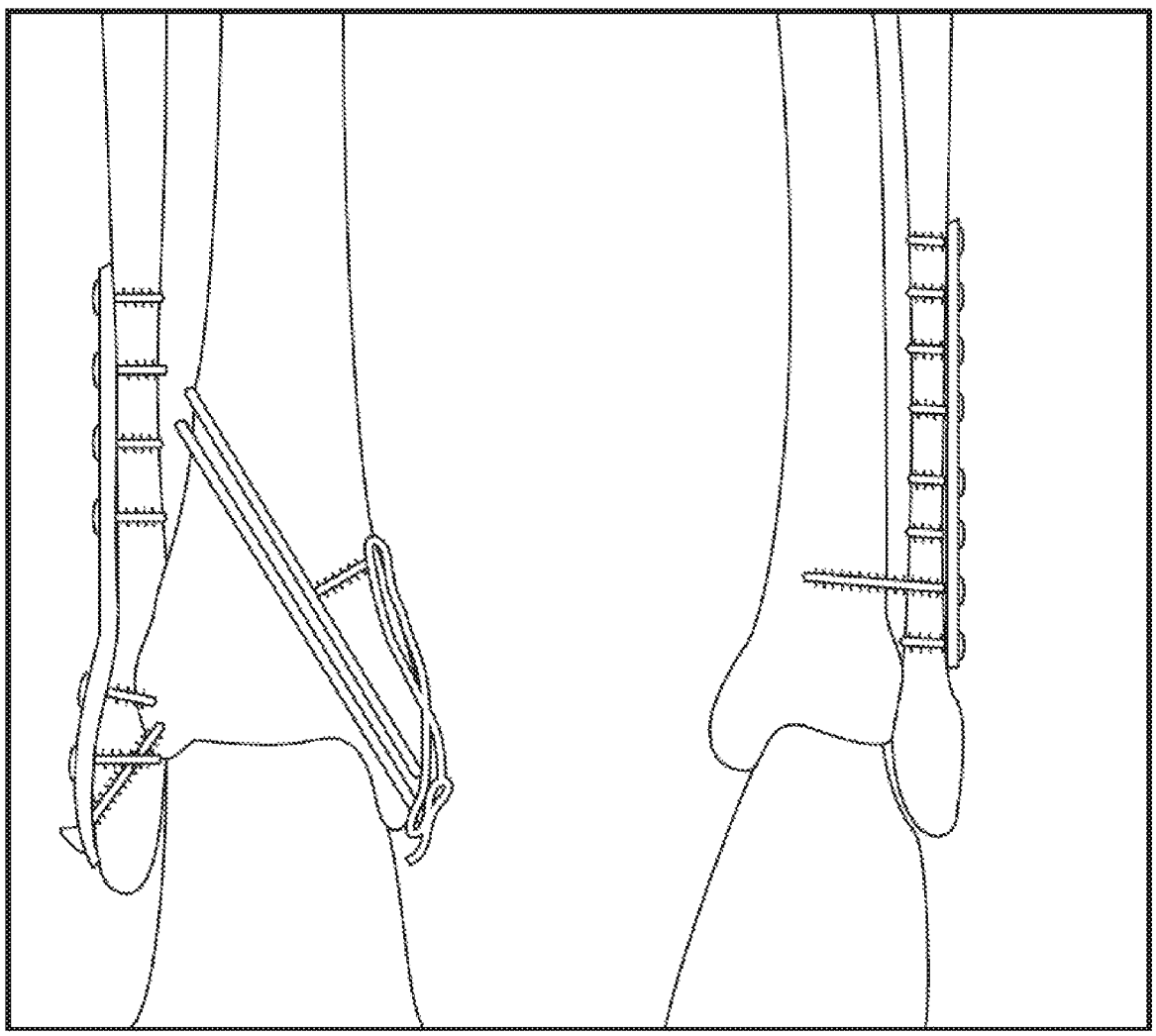
FIG. 5 is a radiograph from the front and the back illustrating the reference locations for a set of screws used in the assembly of a construct for the repair or fusion of an ankle including a distal fibula plate and screws and compression screws angled upward through the medial malleoli into the tibia.
Figure 6:
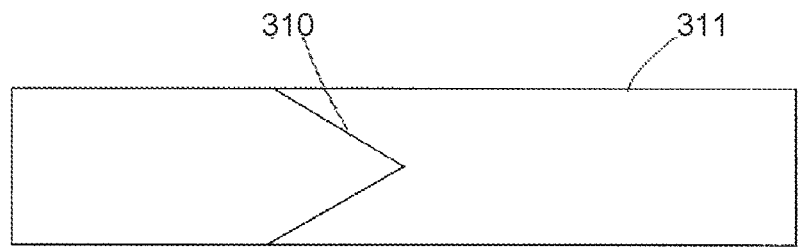
FIG. 6 is a side view illustrating a first distal metatarsal following a chevron cut and re-alignment for repair of Hallus Valgus and prior to the placement of hardware illustrating a step of the method of bunion surgery in accordance with the present invention.
Figure 7:
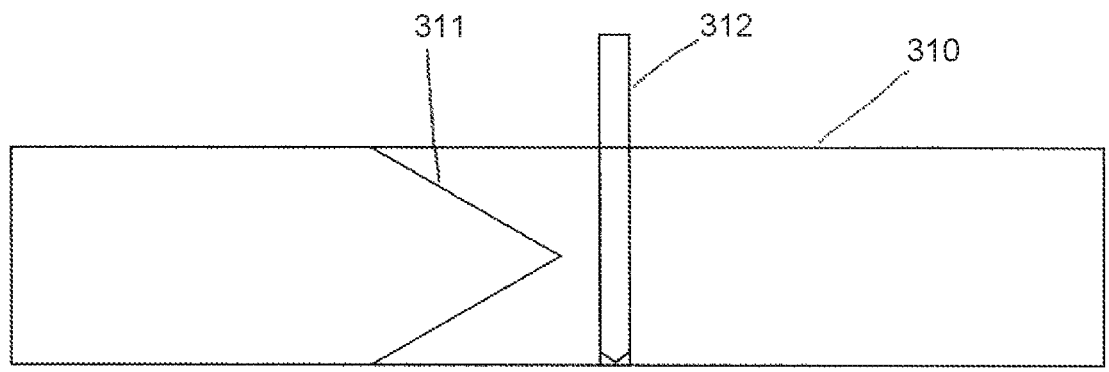
FIG. 7 is a view following the drilling of a hole and insertion of a k-wire along the axis that a fusion screw will intersect of the method of bunion surgery of the present invention.
Figure 8:
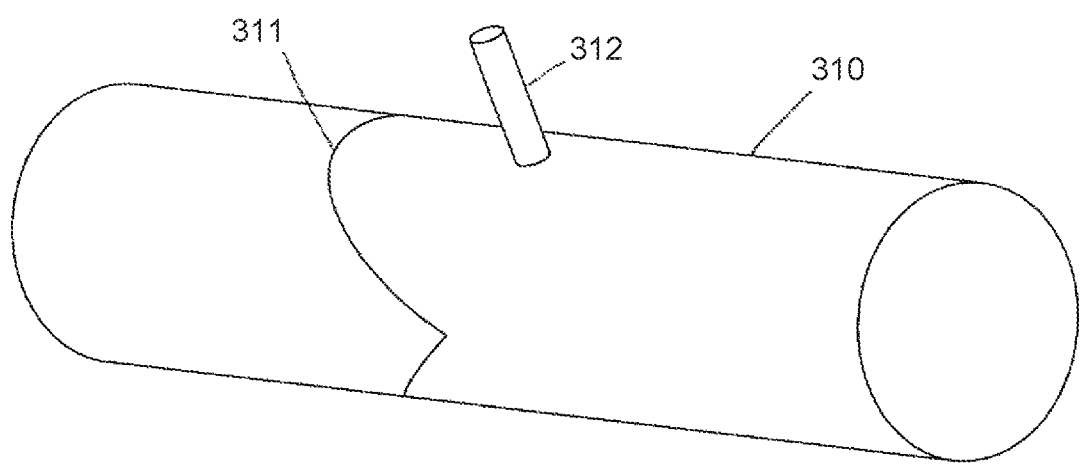
FIG. 8 is an orthographic view of the k-wire in the bone from FIG. 7.
Figure 9:
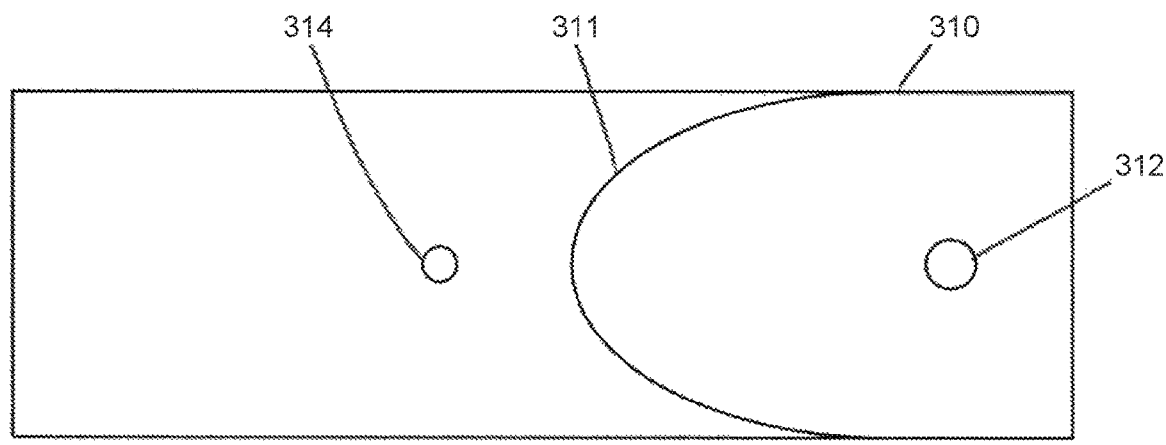
FIG. 9 is an illustration of the location of the fusion screw entry location (the smaller dot and the larger dot represents the K-wire location)
Figure 10:
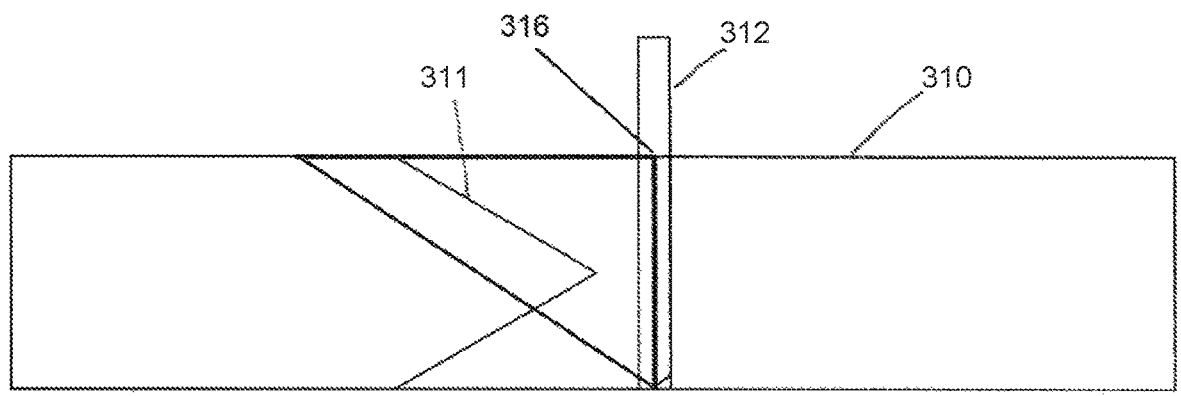
FIG. 10 illustrates the measurement along the axis of the k-wire of the thickness of the metatarsal, which value is recorded as dy.
Figure 11:
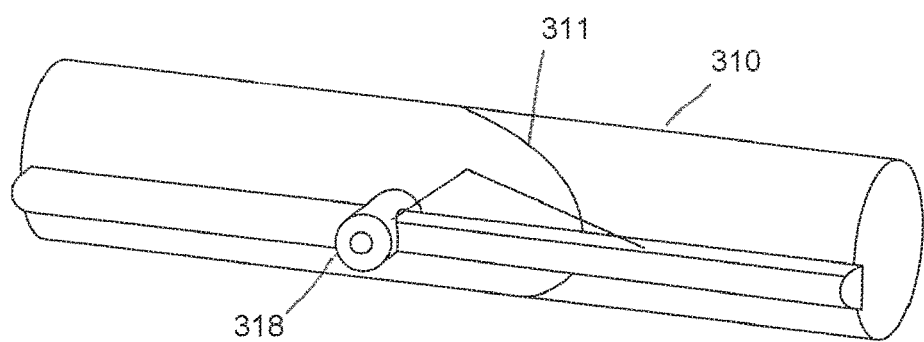
FIG. 11 illustrates a tangible alignment jig (which could be replaced by a virtual version of the jig) placed over the k-wire for measurement of the marked screw entry point along the length of the alignment jig, which value is recorded as the value dx; and wherein the sensor prompts the values of dx and dy for entry into the sensor cluster interface using the display or a remote interface, such as a mobile phone.
Figure 12:
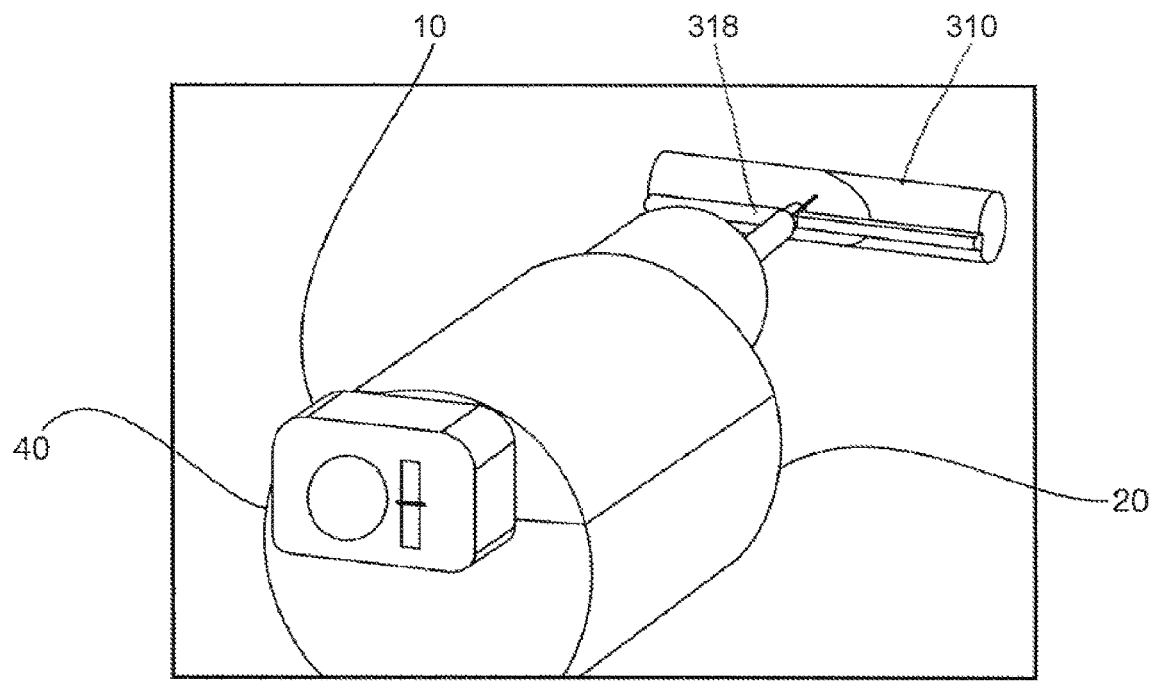
FIG. 12 illustrates the placement of a second embodiment of the instrument in accordance with the invention, in this case, a drill with the attached sensor cluster over the k-wire/alignment jig, and after assuring that the alignment jig is parallel to the line made with the marked screw entry location and the centroid axis of the k-wire, the system is calibrated by pressing the "calibrate alignment" button on the sensor interface.
Figure 13:
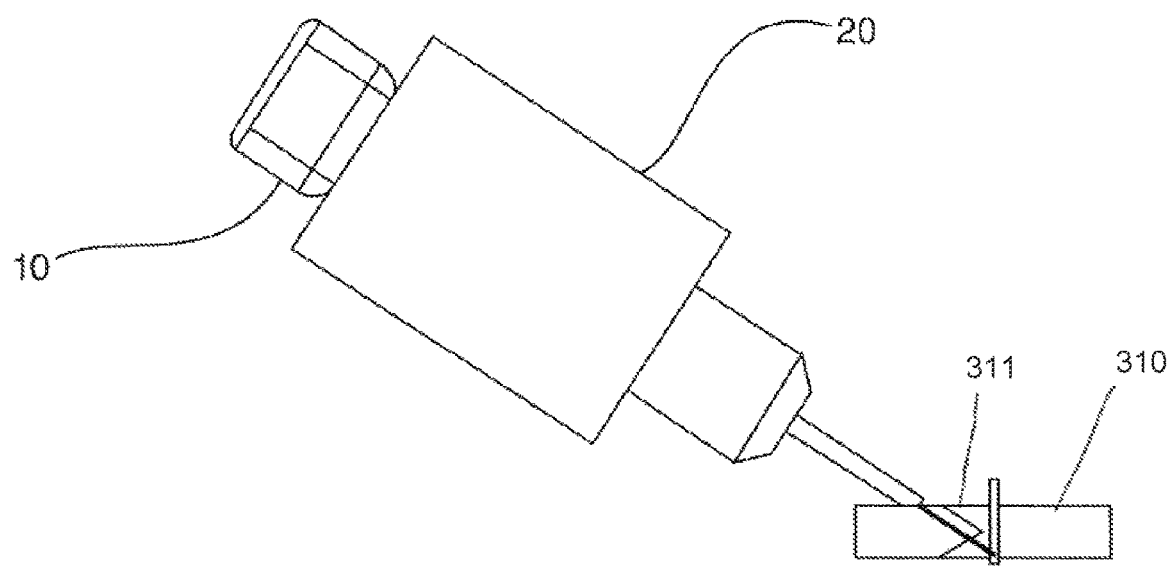
FIG. 13 illustrates the method of the invention in which the instrument with a drill bit in place is aligned to the screw entry location and in which the orientation is displayed on the display screen, in particular by a green circle.
Figure 14:
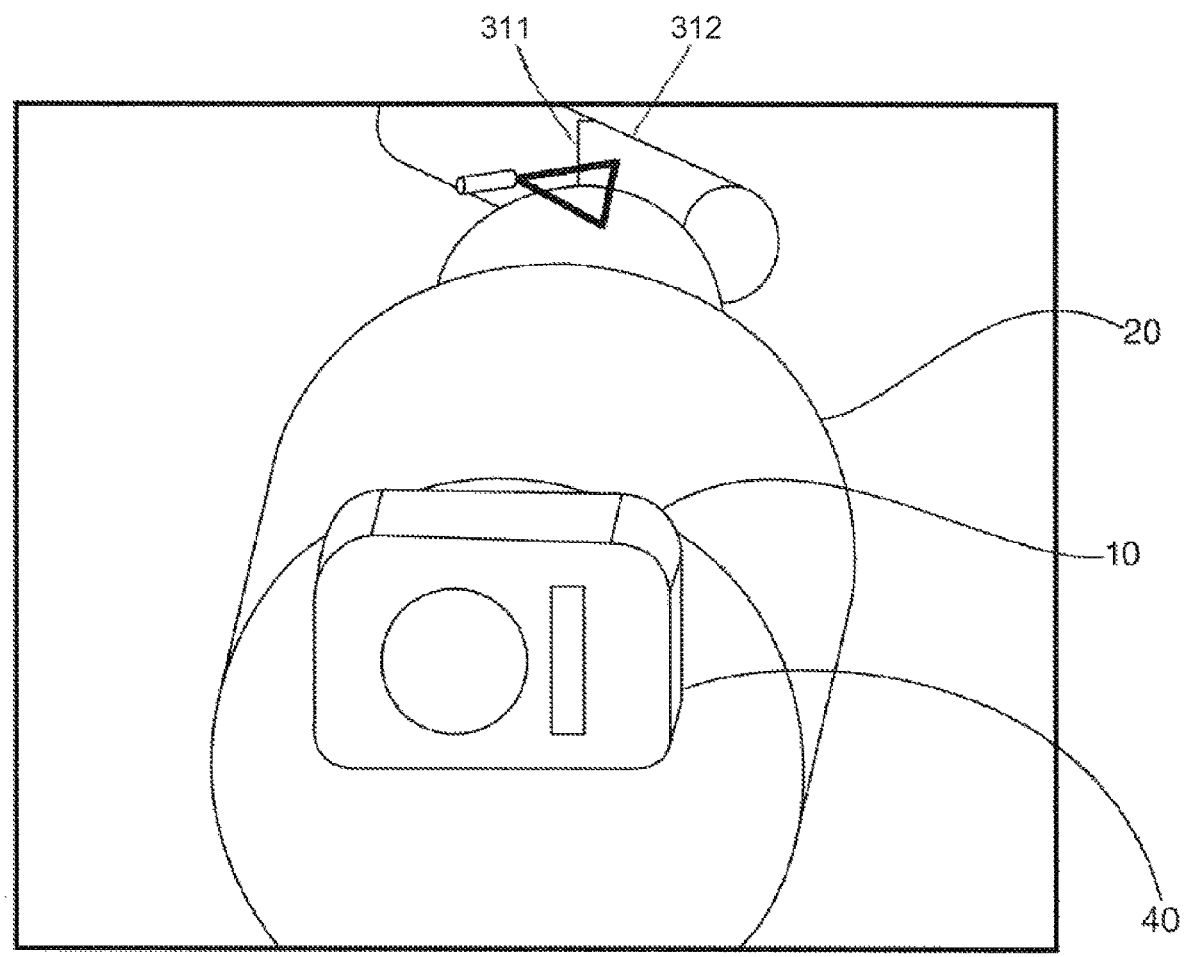
FIG. 14 illustrates the display screen user interface in which the orientation is shown in one GUI, and the depth of work is shown on a second GUI.

The guidance system 10 of the present invention as illustrated in FIG. 3 provides an integrated sensor cluster 12 and integral or separate microprocessor 14 including hardware and software that can aid in the proper targeting for example, for fasteners in general or more specifically for a work piece or a screw, wires or pins, relative to a surgical work area, or for a particular procedure for example for performing an osteotomy. The guidance system 10 is used with a surgical instrument 20, and can be provided separately for attachment to the instrument, or can be built into the instrument. Alternatively, as is convenient, it can be provided as components, such as the display which can be integrated into various surgical tools, or into a separate display, such as glasses or even a mobile device. Since the system is used in surgery, it needs to be able to be sterile so that it can be provided sterile as a sterilized disposable device for a single use, which is attached to a re-usable instrument or it could also be sterilizable, in which case, it could be integrated into the instrument.

The guidance system 10 has a sonar sensor cluster or sensor array 12 that includes at least (and possibly only) a 9 degree of freedom (DOF) three axis accelerometer 32, gyroscope 34, and magnetometer 36 sensor that could be used to track such motion and orientation. This sensor cluster 12 is further integrated into a system that contains a microcontroller 38 and a visual display 40 (preferably both integrated into a single unit, but where the microcontroller 38 or display 40 could be accessed remotely by the sensor cluster, including, for example, on a mobile device, such as a cell phone). The required capabilities of the microprocessor are comparable to the capabilities of the Arduino Mega 2560 microcontroller with a ATmega 2560 microprocessor with 256 KB flash memory, 8 KB of SRAM, 4 KB EEPROM, and a clocking speed of 16 Mhz. Thus, the guidance system is advantageously integrated into or attached to the surgeon's instrument, 20 such as a drill or saw to provide feedback to the surgeon with respect to orientation relative to a defined axis (i.e. "attitude") as well as positional guidance (meaning the ability of the system to direct the surgeon to maintain a desired position during surgery (together, attitude and position comprise a vector). The guidance system 10 defines a reference 100 along with a relative reference position 102, to provide the information required to know the dynamics of the system (i.e. surgical instrument orientation and position relative to the reference position and direction determined from the surgery site.) In order to obtain the real time position, the microprocessor 38 uses the data from the acceleration and mathematically integrates it twice. Since this integration can compound bias error and begin to accumulate position drift, the error signal is compensated for using a defined offset or a specific algorithm in a software component of the invention. Orientation is obtained from integrating the time rate change of angular position (angular velocity) once to obtain the real time angular position and these outputs, the difference in the initial angular position and reference special position can be shown on the display 40 in order to allow the surgeon to perform the orientation and positional corrections needed In order to match the directional output of the GUI 42 on the display 40 of the guidance system10.

The display 40 of the present invention provides a GUI 42 (graphical user interface) which for example, includes a targeting or guidance mechanism 46 such as a spot 47 on a plot 48 (which is advantageously circular) where the surgeon has the goal of centering the spot 47 in the plot 48 to cause the instrument (10 such as a drill or screw driver) to work on axis 104 relative to the defined reference 100. A second GUI provides a bar graph 110, which displays a relative depth (for example for the distal end of a drill tip or a fastener) to provide visual assistance as to the desired amount of penetration of the drill bit or fastener.

As an alternative to, or in addition to the display, the guidance system can include an audio alert system, for example, a series of beeps or buzzing that can either increase or decrease volume, tempo of frequency in order to present information to the guidance user, for example by increasing the tempo as the work piece comes to it's desired location. In addition, the guidance system can include safety means, such as stops to avoid drilling too deep or in the wrong location.

Figure 15:
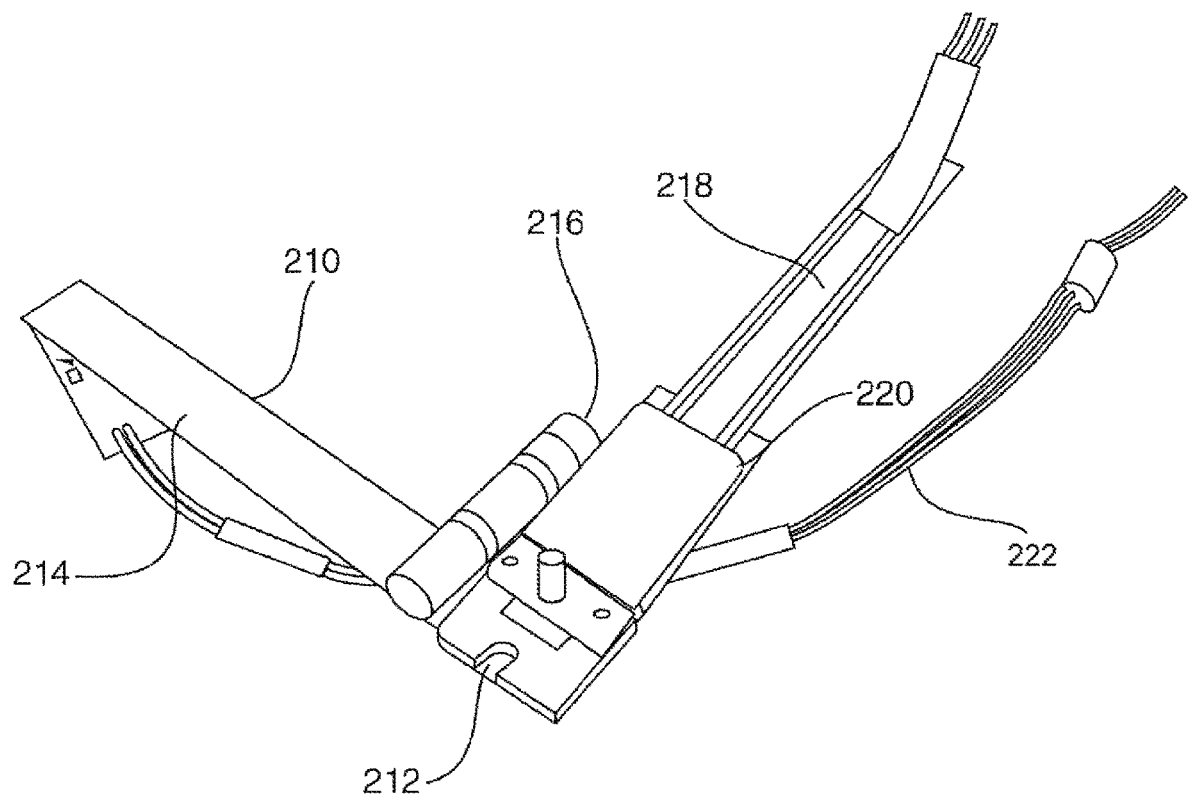
FIG. 15 illustrates a further embodiment of a jig that can be used to help define the local coordinate system of the present invention.

In further embodiment, the mechanical jig 210 that is illustrated in FIG. 15 has an opening or bore 212 which captures a guide wire to define a first axis extending along the axis of the opening 212 and defined by the interior side walls of the opening. A first arm 214 extends at a first right angle to the opening, and includes a level, such as the bubble level 216 to ensure that the jig is level. An orthogonal sliding arm 218 is provided and is provided with hatch marks to provide a visual indication of a defined length along the second arm 218. Optionally arm 214 can be provided with a mechanism for translating the arm along the axis of arm 218 without changing the angle between the two arms in order to provide an optimal geometry for associated sensors, such as linear potentionmeters. The jig is provided with one, two or more 100 mm 10 kOhm linear potentiometers 220, and is connected, such as by a wired 222 or a wireless connection to the microprocessor of the system. Ideally, the potentiometers are located on different arms of the jig to verify the relative location of the coordinate system, and the k-wire may also include a potentiometer (i.e. a third one) here to mark that distance as well. The jig may include an offset from the bone to accommodate the anatomy as desired.

As a further aspect of the invention, a method of surgery is provided which relates generally to surgery in which a MEMS sensor guidance system 10 is mounted on an instrument 20 and which uses the MEMS sensor 12 to determine Inertial Measurement Units to track rotation and acceleration in all three spatial directions. One such method of surgery is illustrated as a chevron cut bunionectomy, although it is understood that it can be used for other surgeries, for example, for fusion such as for the placement of a compression screw, or for any small or long bone or spinal or maxofacial surgery, for example using a plate or implant that is fixed relative to a bone or bones, by a fastener, such as a screw, or many other surgical procedures.

In accordance with this method, the surgical area is prepped, such as for example by excision to allow access to the area for surgical intervention (or in the case of minimally invasive surgery to allow an implant to be placed without a fully opened incision). Next, a reference axis is set, for example by drilling a pilot hole, in the bone 310 (having a chevron incision 311) and inserting a k-wire 312 such as along an axis which a fastener will intersect and defining a reference axis by registering two points on the k-wire at a known spaced distance, in the memory of the microprocessor. Next, a loci is defined, for example, an entry point 314 for a fastener 316; and a depth is determined by measuring a boundary distance for the intervention (e.g., when a fastener will be inserted into a bone segment, the thickness of the bone is measured which represents the depth beyond which the surgeon does not wish to penetrate in order to avoid disturbing the soft tissue beyond the cortical surface on the back side of the bone segment). This depth is recorded in a memory of the microprocessor of the instrument in accordance with the invention as a value, dy. Next, a value is determined along an orthogonal axis, x, which can be determined using an actual horizontal jig 318 that includes an indication for a fastener entry hole, or by a virtual version of the jig for example utilizing a reflected light beam instead of the metal jig and wherein the virtual jig is provided in the microprocessor of the instrument. Then, the instrument preferably including the sensor cluster of the invention is placed in relation to the y-axis and x-axis and the device is calibrated using the button marked "calibrate alignment" on this sensor interface display, after assuring that the axes are properly aligned, for example by checking to be sure that the alignment jig is parallel to the line made with the marked fastener entry location and the centroid axis of the k-wire. Then, with the instrument in place, the working end is aligned to the area of intervention, for example, for a drill, the distal end of the drill bit in the drill is aligned to the fastener entry location and the orientation data is displayed on the display screen such as by a green circle, and the fastener orientation is determined and maintained by aligning a fastener icon displayed on the instrument sensor cluster screen in the proper positioning on the alignment marker and by monitoring the degree of work on the secondary work monitor, for example on a graphical representation of the depth or degree of penetration in the Y-axis. This procedure helps to ensure the optimal placement for surgical intervention, for example, for the placement of a pilot hole in order to assure the subsequent alignment and full seating of a fastener, such as a screw having a threaded locking head in relation to a projected internally threaded locking screw hole in an orthopedic implant. As final steps of the method in accordance with the invention, the alignment is repeated as necessary for the placement of all fasteners, and the surgical access or incision is closed.

The method of the present invention is particularly advantageous for use in minimally invasive procedures, and procedures in which fasteners are introduced percutaneously, or through the skin.

In accordance with the present invention, various procedures can be performed with the assistance of the instrument guidance system, including for example, inserting fasteners including with up-loaded specific information as to the relative location of a plurality of fasteners or of the relative location of bone fragments for typical fracture patterns, or in the case of reconstruction, the angle of incision for example by maneuvering the desired axis over time, since the present system has the advantage of allowing a rate change of orientation to be monitored. Likewise, the device can be used to access patient specific information, which might be gathered on the basis of pre-surgical imaging including for example, fluoroscopy, MRI, tomography and x-ray imaging.

While in accordance with the patent statutes the best mode and preferred embodiment have been set forth, the scope of the invention is not limited thereto, but rather by the scope of the attached claims.

What is claimed is:

1. A method of surgery on a bone within an anatomical area using a surgical guidance system comprising the steps of:
    setting a reference axis which is used to define a reference vector and registering the reference vector in the anatomical area which includes the bone to establish a local three-dimensional reference coordinate system for the bone and for the surgical guidance system,
    the surgical guidance system comprising a hand-held surgical drill, a wire driver, or a screw driver having a tool which is aligned and operates along a linear tool work axis and one or more mount which supports a six degree of freedom Inertial Measurement Unit (IMU) sensor or sensors comprising an Micro Electro-Mechanical System (MEMS) device which tracks global based location information of the tool axis to define a tool vector in the local three-dimensional reference coordinate system, the globally-based location information comprising the angular position, the rotation and the acceleration of the tool vector relative to the bone in three-dimensions in the local three-dimensional reference coordinate system, and the surgical guidance system further including a microprocessor coupled to a receiver that receives the globally-based location information from the sensor and the surgical guidance system and having a memory loaded with machine readable code to calculate an attitude and position of the tool vector from the globally-based location information, and a display;
    using fluoroscopy intra-operatively to establish and define a loci in the local three-dimensional reference coordinate system which represents an entry point or end point for the tool on the bone;
    introducing the tool into the local three-dimensional reference coordinate system at the entry point and calibrating the alignment at the entry point of the tool vector relative to local three-dimensional reference coordinate system; and
    monitoring the attitude and position of the tool vector relative to the local three-dimensional reference coordinate system, and the location of the tool vector relative to the loci on the display using the surgical guidance system in order to perform a surgical procedure.

2. A method of surgery as set forth in claim 1 wherein the surgery is a minimally invasive surgery.

3. A method of surgery as set forth in claim 1 wherein the reference vector is set by drilling a pilot hole and inserting a pin along the reference vector which is coincident with the reference vector and recording the location of the reference vector in the memory of the guidance system.

4. A method of surgery as set forth in claim 3 wherein two points on the pin at a pre-determined spaced distance are registered in the memory of the guidance system in order to register the reference vector.

5. A method of surgery as set forth in claim 4 wherein the loci represents the location for an entry point for a fastener.

6. A method of surgery as set forth in claim 5 further including the step of defining a boundary distance from the loci and wherein the boundary distance is a depth.

7. A method of surgery as set forth in claim 6 wherein the depth is based on the thickness of a bone.

8. A method of surgery as set forth in claim 7 wherein the depth is recorded in a memory of the microprocessor as a value, dy.

9. A method of surgery as set forth in claim 8 wherein a value, dx, is determined along an axis, x which is orthogonal to the direction of the depth.

10. A method of surgery as set forth in claim 9 wherein the local three-dimensional reference coordinate system vector x is determined using a horizontal jig.

11. A method of surgery as set forth in claim 10 wherein the jig is a virtual jig.

12. A method of surgery as set forth in claim 11 wherein the jig includes an indication for one or more fastener holes in an implant.

13. A method of surgery as set forth in claim 12 wherein the jig uses a reflected light beam and is provided in the microprocessor.

14. A method of surgery as set forth in claim 1 further including the step of calibrating the guidance system by assuring that the reference vector and the tool vector are properly aligned and recording the calibration in the memory of the system.

15. A method of surgery as set forth in claim 14 wherein the tool is aligned to a fastener entry location and orientation data is displayed on the display screen.

16. A method of surgery as set forth in claim 15 wherein a graphical user interface is provided on a display which includes a marker and a two dimensional matrix and the marker is aligned in the two dimensional matrix during the surgery.

17. A method of surgery as set forth in claim 16 wherein the surgery involves the placement of a fastener having an orientation, and the fastener orientation is determined and maintained by aligning the marker and the orientation in the two dimensional matrix.

18. A method of surgery as set forth in claim 17 further including a secondary work monitor including the step of displaying a degree of work on the secondary work monitor.

19. A method of surgery as set forth in claim 18 wherein the secondary work monitor indicates the depth of penetration of the tool in a Y-axis of the local three-dimensional reference coordinate system.

20. A method of surgery as set forth in claim 1 wherein the surgical guidance system further includes an audio indication of the orientation of the tool.

21. A method of surgery as set forth in claim 1 wherein the tool is a locking screw in an implant.

22. A method of surgery as set forth in claim 1 wherein the surgical guidance system includes a computer processor and a computer readable medium that acts as a communication receiver which can receive and convert to memory data.

23. A method of surgery as set forth in claim 22 wherein the data is one or more of data regarding the placement of multiple fasteners, data as to specific surgical procedures and patient specific data.

24. A method of surgery as set forth in claim 1 further including the step of using a visual image in conjunction with the surgical guidance system.

25. A method of surgery as set forth in claim 24 wherein the visual image is captured using fluoroscopy.

26. A method of surgery as set forth in claim 25 wherein the visual image is used to verify the coordinate system or a scale of the coordinate system.

27. A method of surgery as set forth in claim 1 wherein the surgical guidance system can be sterilized.

28. A method of surgery as set forth in claim 1 wherein the tool interacts with an implant and the implant has a depth in the bone and wherein the depth of the implant is determined digitally so as to preclude the use of less precise mechanical measuring means.

29. A method of surgery as set forth in claim 1 wherein the surgery is a biopsy.

30. A method of surgery on a bone within an anatomical area comprising the steps of:
    setting a reference axis to define a reference vector and registering the reference vector in the anatomical area which includes the bone to establish a local three-dimensional reference coordinate system for the bone and for a surgical guidance system;
    the surgical guidance system comprising a hand-held surgical instrument having a tool aligned along a tool work axis which is used to define a tool vector and a mount which supports at least a six degree of freedom Inertial Measurement Unit (IMU) sensor which tracks global based location information comprising the angular position, the rotation and the acceleration, in three-dimensions of the tool vector in the local three-dimensional reference coordinate system relative to the bone, and the surgical guidance system further includes a microprocessor coupled to a receiver that receives the globally-based location information from the sensor and the surgical guidance system and having a memory loaded with machine readable code to calculate a position of the workpiece tool vector from the globally-based location information and a display;
    using fluoroscopy intra-operatively to define a loci which represents an entry point or end point of the tool on the bone and within the local three-dimensional reference coordinate;
    introducing the tool into the local three-dimensional reference coordinate system at the entry point and calibrating the alignment of the tool vector relative to local three-dimensional reference coordinate system; and
    monitoring the position of the tool vector relative to the local three-dimensional reference frame and the location of the tool vector relative to the loci and showing the position of the tool vector on the display using the surgical guidance system in order to perform a surgical procedure.

31. A method of surgery on a bone as set forth in claim 30 further comprising the step of monitoring the trajectory of the tool vector relative to the local three-dimensional reference frame as it progresses from a start point to an end point.

* * * * *